(12) United States Patent
Chen

(10) Patent No.: US 9,835,530 B1
(45) Date of Patent: Dec. 5, 2017

(54) MANUFACTURING METHOD OF EMBEDDED SAMPLE BLOCK AND SAMPLE SHEET

(71) Applicant: BIO MATERIALS ANALYSIS TECHNOLOGY INC., Hsinchu County, TN (US)

(72) Inventor: Hung-Jen Chen, Hsinchu (TW)

(73) Assignee: BIO MATERIALS ANALYSIS TECHNOLOGY INC., Hsinchu County (TW)

( * ) Notice: Subject to any disclaimer, the term of this patent is extended or adjusted under 35 U.S.C. 154(b) by 0 days.

(21) Appl. No.: 15/331,917

(22) Filed: Oct. 24, 2016

(30) Foreign Application Priority Data

Sep. 8, 2016 (TW) .............................. 105129166 A

(51) Int. Cl.
*G01N 1/36* (2006.01)
*H01J 37/26* (2006.01)

(52) U.S. Cl.
CPC ................ *G01N 1/36* (2013.01); *H01J 37/26* (2013.01); *G01N 2001/364* (2013.01); *G01N 2001/366* (2013.01)

(58) Field of Classification Search
CPC . H01J 37/20; H01J 37/26; G01N 1/28; G01N 1/2806; G01N 1/2813; G01N 1/36
See application file for complete search history.

(56) References Cited

U.S. PATENT DOCUMENTS

| 2010/0009431 | A1 | 1/2010 | Cho et al. | |
|---|---|---|---|---|
| 2013/0087945 | A1* | 4/2013 | Kusters | G01N 1/36 264/275 |
| 2014/0212913 | A1* | 7/2014 | Ohta | C08L 63/00 435/29 |
| 2015/0008616 | A1* | 1/2015 | Pasternak | G01N 1/36 264/275 |

FOREIGN PATENT DOCUMENTS

| CN | 102614946 | | 11/2014 | |
|---|---|---|---|---|
| KR | 2013131569 | A * | 12/2013 | ............... G01N 1/28 |
| TW | 200606413 | | 2/2006 | |

OTHER PUBLICATIONS

"Office Action of Taiwan Counterpart Application," dated Mar. 17, 2017, p. 1-p. 3.

* cited by examiner

*Primary Examiner* — David E Smith
(74) *Attorney, Agent, or Firm* — JCIPRNET

(57) ABSTRACT

A manufacturing method of an embedded sample block includes providing a carrier. The carrier has a sample accommodating area and a marking area. The sample accommodating area has a first groove and the marking area has second grooves. A sample is disposed in the first groove and a molding plate standing around the carrier is formed. The molding plate surrounds the sample accommodating area and the marking area and forms an opening exposing the sample, the first groove and the second grove. A molding material is formed inside the opening, such that the molding material covers the sample and is filled into the first and (Continued)

second grooves. The molding material is solidified and the molding plate is removed to obtain the embedded sample block. In addition, a sample sheet sliced from the embedded sample block is also mentioned.

15 Claims, 17 Drawing Sheets

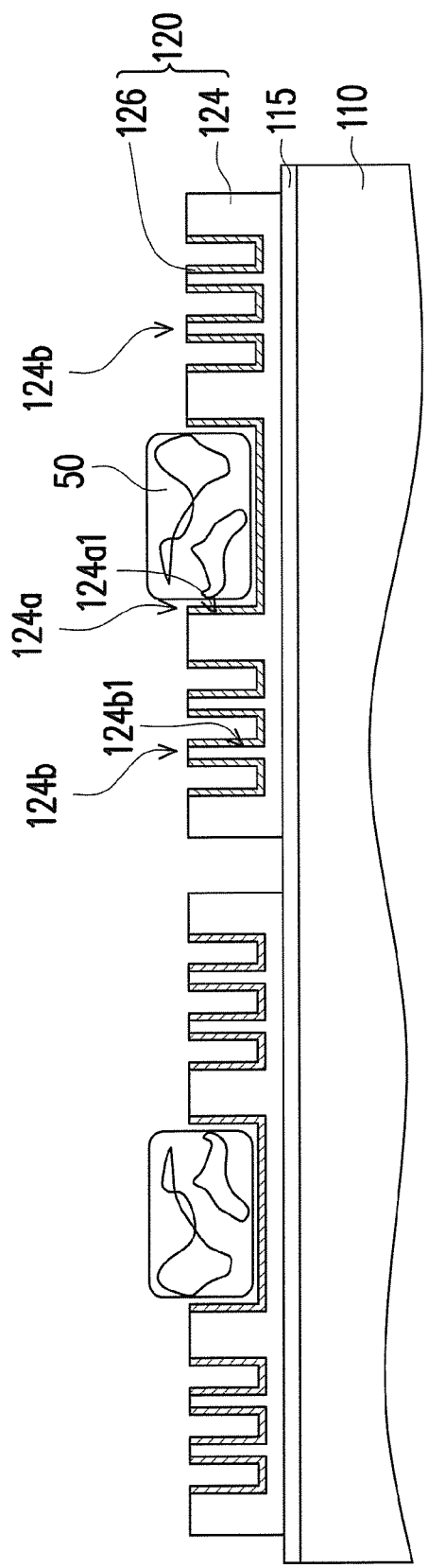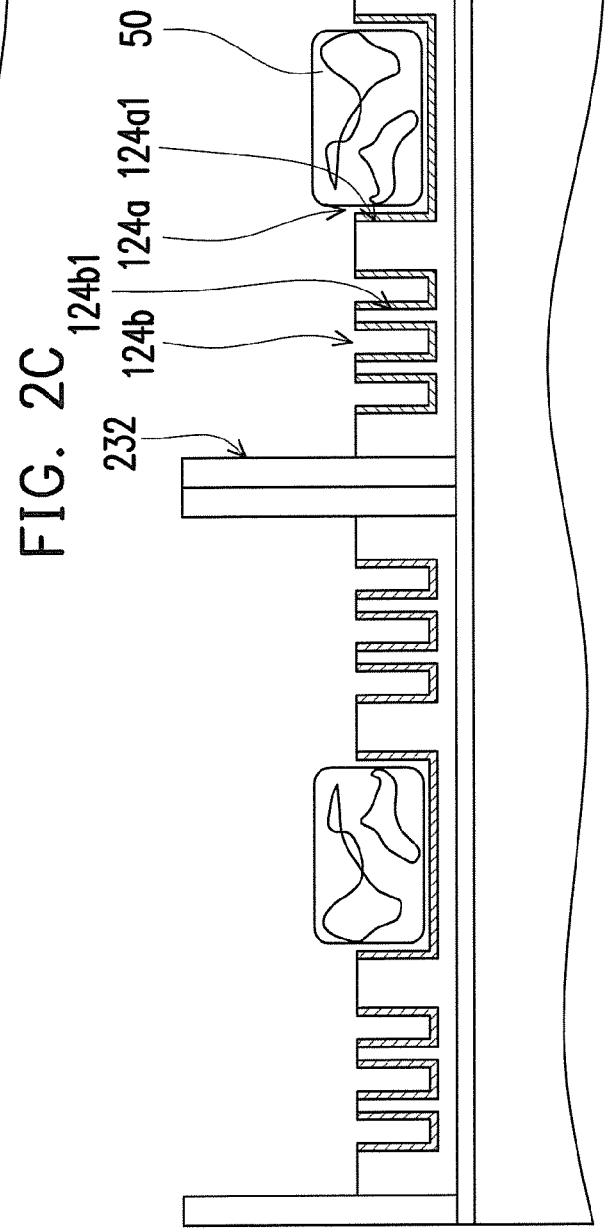

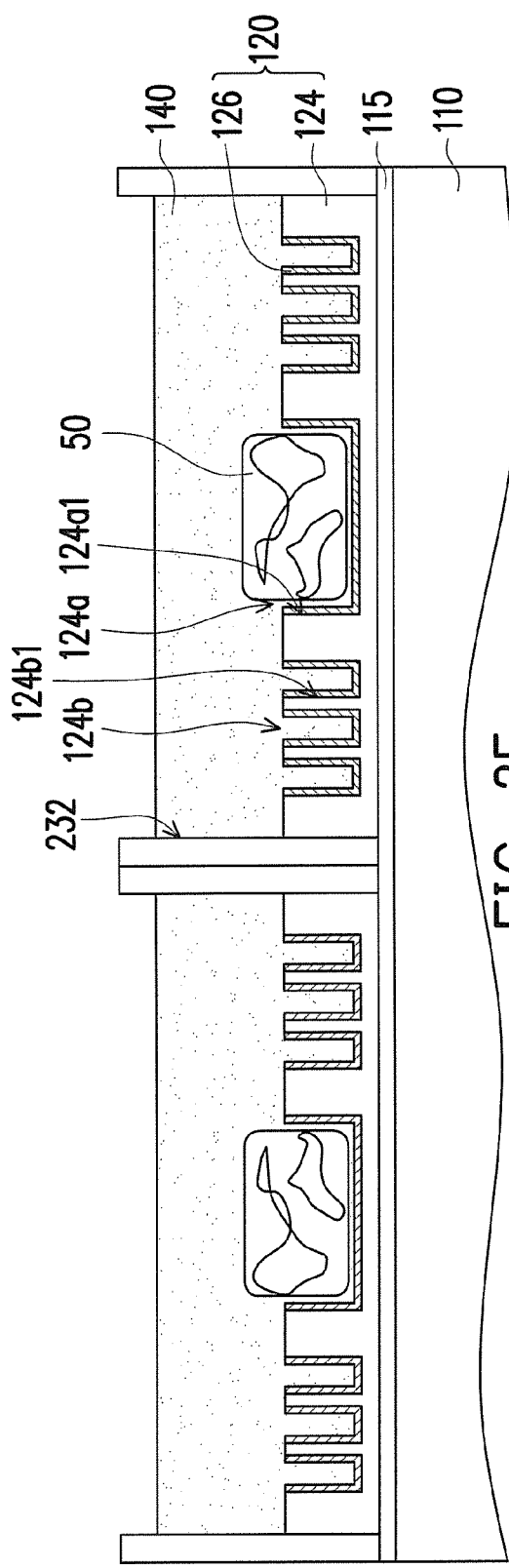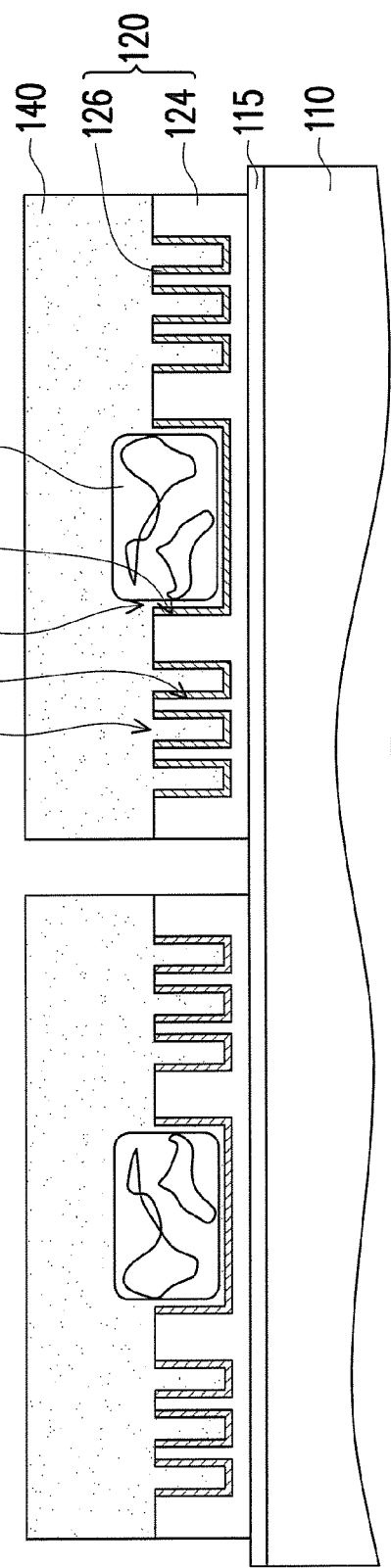
FIG. 2E
FIG. 2F

MANUFACTURING METHOD OF EMBEDDED SAMPLE BLOCK AND SAMPLE SHEET

CROSS-REFERENCE TO RELATED APPLICATION

This application claims the priority benefit of Taiwan application serial no. 105129166, filed on Sep. 8, 2016. The entirety of the above-mentioned patent application is hereby incorporated by reference herein and made a part of this specification.

BACKGROUND

1. Field of the Invention

The disclosure relates to a sample of an electron microscope, and particularly relates to a manufacturing method of an embedded sample block of an electron microscope.

2. Description of Related Art

The high-resolution three-dimensional image technologies of the electron microscopes have been applied in the analyses and tests for clinical medical studies and bimolecular research, and such application effectively increases the resolution of the image under observation and the accuracy of the observed result. However, during the process of establishing the high-resolution three-dimensional image, a significant amount of ultra-thin samples need to be prepared, and the image requires precise positioning during the process of observing the samples. In the conventional manufacturing process of a sample block for the electronic microscope, it is still the majority to manually resin-embed each sample by using an embedding capsule. Thus, when a large amount of samples need to be observed, it is time and labor consuming to manufacture the samples. Also, the quality of the sample manufactured each time may differ, making the qualities of the samples under observation inconsistent. Consequently, the quality of the observation on the samples may be affected. Thus, how to effectively facilitate the efficiency and quality of the manufacture of the sample block for the electron microscope has become an important issue in the development of the electron microscope observation technologies nowadays.

SUMMARY

The disclosure provides a manufacturing method of an embedded sample block capable of manufacturing the embedded sample block having a mark to align samples by batch manufacturing, so as to increase an efficiency and quality of manufacturing samples for an electron microscope.

The disclosure provides a sample sheet formed by continuously slicing an embedded sample block. In addition, a mark is provided on a surface of a sample slice, and the mark may be used for alignment. With the sample sheet, the time required for an electron microscope to position the sample sheet and reorganize an image during observation on sample sheets may be saved.

A manufacturing method of an embedded sample block according to an embodiment of the disclosure includes: providing a carrier having a sample accommodating area and a marking area, wherein the sample accommodating area has a first groove, and the marking area has a plurality of second grooves; disposing a sample in the first groove; forming a molding plate standing around the carrier, wherein the molding plate surrounds the sample accommodating area and the marking area and forms an opening exposing the sample, the first groove, and the second grooves; forming a molding material inside the opening, wherein the molding material covers the sample and is filled into the first groove and the second grooves; curing the molding material and removing the molding plate to obtain the embedded sample block.

A sample sheet according to an embodiment of the disclosure is obtained by continuously slicing an embedded sample block along an axial direction. Profiles of different sample sheets correspond to cross-sectional profiles of the embedded sample block at different positions in the axial direction, so as to determine a sequence of the respective sample sheets. The embedded sample block includes a carrier, a sample, a molding material, and a carrying part. The carrier has a sample accommodating area and a marking area. The sample accommodating area has a first groove, and the marking area has a plurality of second grooves. The sample is disposed in the first groove. The molding material covers the sample and is filled into the first groove and the second grooves. The sample sheet includes a carrying part, a sample slice, and a molding part. The carrying part is obtained by slicing the carrier. The carrying part has an accommodating hole corresponding to the first groove and a plurality of marking holes corresponding to the second grooves. The sample slice is located in the accommodating hole. The molding part is filled into the accommodating hole and the marking holes.

According to an embodiment of the disclosure, the step of forming the carrier includes: providing a carrier material layer on the substrate; forming a release layer between the carrier material layer and the substrate, such that the carrier material layer is disposed above the substrate with interposition of the release layer; patterning the carrier material layer to form the first groove and the second grooves; and forming a marking layer covering surfaces of the first groove and the second grooves.

According to an embodiment of the disclosure, the step of patterning the carrier material layer includes: forming a patterned mask on the carrier material layer; and etching the carrier material layer by using the patterned mask, so as to form the first groove and the second grooves.

According to an embodiment of the disclosure, the step of forming the patterned mask includes: coating a photoresist layer on the carrier material layer; patterning the photoresist layer; and curing the patterned photoresist layer to form the patterned mask.

According to an embodiment of the disclosure, the manufacturing method of the embedded sample block further includes polishing a bottom surface of the embedded sample block to expose a portion of the marking layer and form marks.

According to an embodiment of the disclosure, the step of forming the carrier includes: providing a substrate; patterning a surface of the substrate to form the first groove and the second grooves; and forming a marking layer covering surfaces of the first groove and the second grooves.

According to an embodiment of the disclosure, the manufacturing method of the embedded sample block further includes slicing the embedded sample block along an axial direction to form a plurality of sample sheets.

According to an embodiment, the opening is in a trapezoid shape, a doubly-truncated circular shape, or a polygonal shape.

According to an embodiment of the disclosure, a width of the first groove gradually decreases along the axial direction.

According to an embodiment of the disclosure, a width of the first groove of the embedded sample block gradually decreases along the axial direction, and the accommodating holes of different sample sheets have different widths.

According to an embodiment of the disclosure, profiles of the sample sheets include a trapezoid shape, a doubly-truncated circular shape, or a polygonal shape.

According to an embodiment of the disclosure, the molding material includes resin.

According to an embodiment of the disclosure, the carrier includes a marking layer. The marking layer covers surfaces of the first groove and the second grooves. The carrying part of the sample sheet has marking rings located in the respective marking holes and corresponding to the marking layer.

According to an embodiment of the disclosure, the marking holes of the sample slices have the same layout.

Based on the above, in the manufacturing method of the embedded sample block according to the embodiments of the disclosure, the carrier material layer of the embedded sample block has the sample accommodating area and the marking area, such that the embedded sample block may be sliced into the sample sheets whose surfaces are provided with marks. In the embodiments of the disclosure, since the embedded sample block may be sliced into the sample sheets, the efficiency of manufacturing the samples for the electron microscope is significantly increased, and the manufacturing qualities of the sample sheets to be observed with the electron microscope may tend to be consistent. Also, since the marks are directly manufactured on the sample sheets, the mark may be used for alignment, such that the time required to position the sample during observation and reorganize an image may be significantly reduced.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIGS. 2A to 2G are schematic views illustrating a manufacturing method of an embedded sample block according to another embodiment of the disclosure.

DESCRIPTION OF THE EMBODIMENTS

Figure 1A:
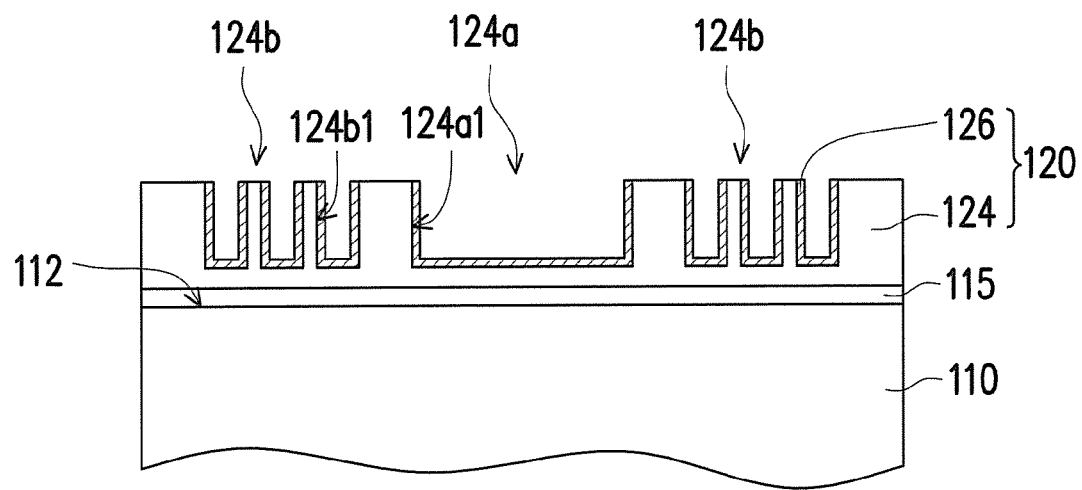
FIGS. 1A to 1G are schematic views illustrating a manufacturing method of an embedded sample block according to an embodiment of the disclosure.

Reference will now be made in detail to the present preferred embodiments of the disclosure, examples of which are illustrated in the accompanying drawings. Wherever possible, the same reference numbers are used in the drawings and the description to refer to the same or like parts.

FIGS. 1A to 1G are schematic views illustrating a manufacturing method of an embedded sample block according to an embodiment of the disclosure. Referring to FIG. 1A to 1G, a manufacturing method of an embedded sample block 100 includes providing a carrier 120 (as shown in FIG. 1A). In this embodiment, the carrier 120 includes a carrier material layer 124 and a marking layer 126. The carrier 120 may be disposed on a substrate 110, and a material of the substrate 110 includes a silicon wafer, for example. Then, as shown in FIG. 1A, a release layer 115 may be formed between an upper surface 112 of the substrate 110 and the carrier material layer 124. Thus, the carrier material layer 124 may be disposed above the substrate 110 with interposition of the release layer 115.

In this embodiment, a material of the release layer 115 includes a layered aluminum material, for example, and a material of the carrier material layer 124 includes a layered resin material, for example. However, in the embodiments of the disclosure, the material of the release layer 115 is not limited thereto. In other embodiments, the material of the release layer 115 may further include a titanium (Ti) layer, a chromium (Cr) layer, a gold (Au) layer, a platinum (Pt) layer, or a metal compound material layer, such as an aluminum oxide ($Al_2O_3$) layer, a titanium oxide ($TiO_2$) layer, a tantalum oxide ($Ta_2O_4$) layer, and the like, for example. Besides, the material of the carrier material layer 124 is not limited to the above. In other embodiments, the material of the carrier material layer 124 may also include a polymer layer, such as a resin layer, a photoresist layer, a polyimide (PI) layer, a polymethylmethacrylate (PMMA) layer, or an inorganic dielectric material layer, such as a silicon oxide layer, a silicon nitride layer, or the like.

In this embodiment, the carrier 120 includes a sample accommodating area 124a and a marking area 124b. The sample accommodating area 124a includes a first groove 124a1, and the marking area 124b includes a plurality of second grooves 124b1. As shown in FIG. 1, a marking layer 126 may be formed on surfaces of the first groove 124a1 and the second grooves 124b1 by performing a sputtering process. In addition, a material of the marking layer 126 includes a gold layer or an aluminum layer, for example.

Figure 1B:
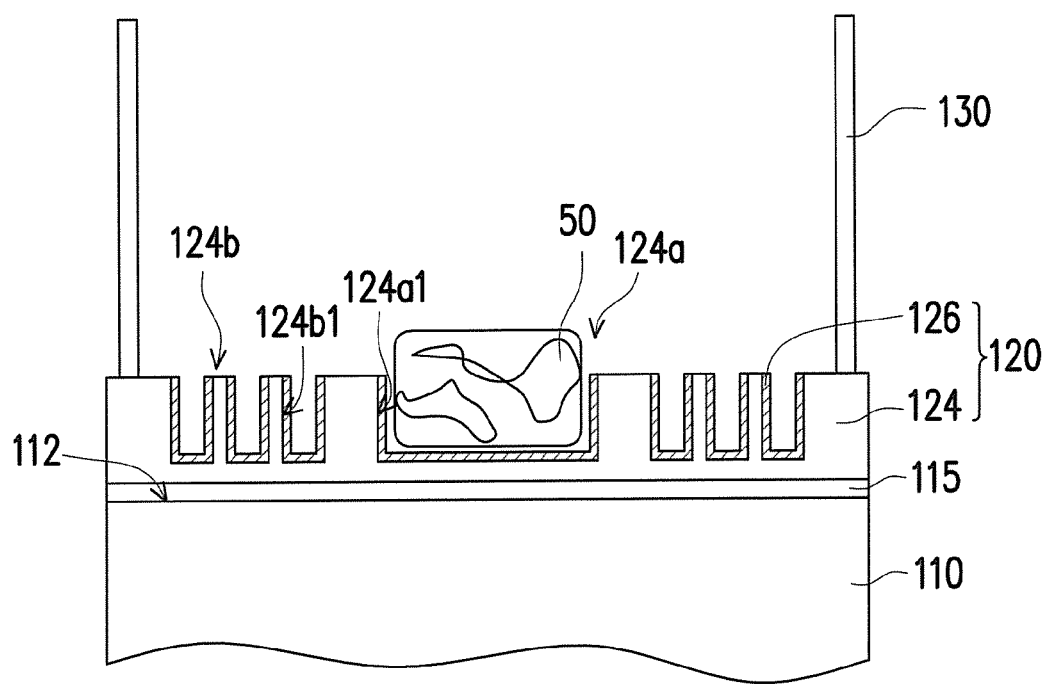

Then, referring to FIG. 1B, a sample 50 may be disposed in the first groove 124a1. In this embodiment, a molding plate 130 may be disposed around the carrier 120. An extending direction of the molding plate 130 is perpendicular to a planar direction of the upper surface 112 of the substrate 110, and the molding plate 130 surrounds the sample accommodating area 124a and the marking area 124b, so as to form an opening exposing the first groove 124a1 and the second grooves 124b1. In this embodiment, a structure of the molding plate 130 may be manufactured by using a material compatible with a manufacturing process of a semiconductor or micro-electromechanical element, such as a silicon wafer or a glass wafer. Alternatively, in other embodiments, the structure of the molding plate 130 may also be manufactured by processing a material such as ceramics, quartz, or a plastic block, for example.

Figure 1C:
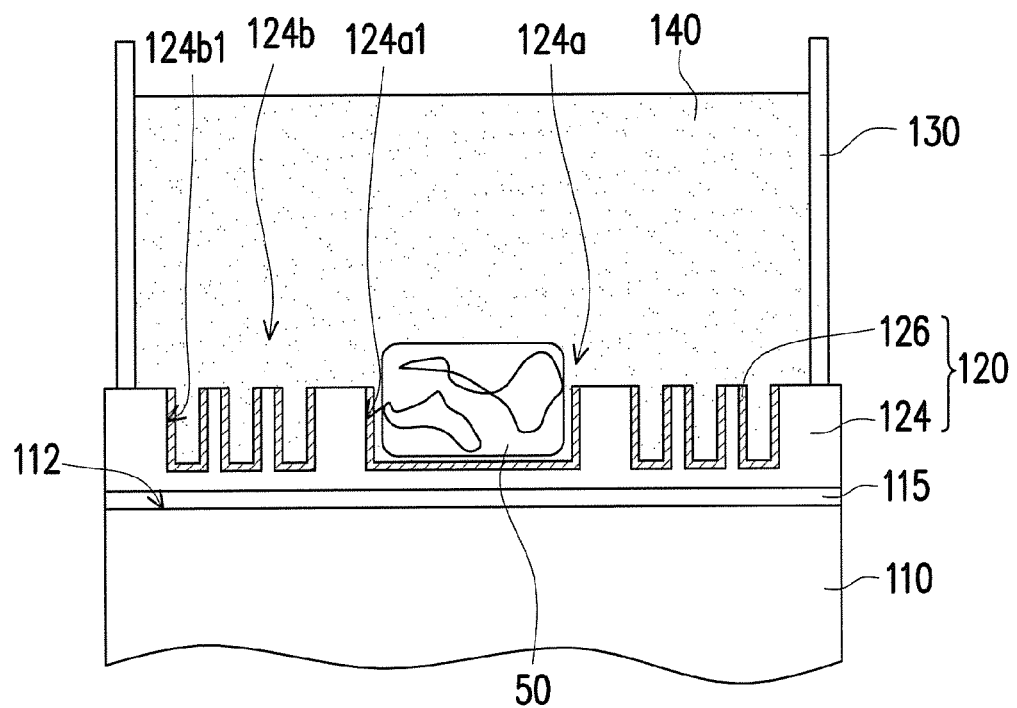
Figure 1D:
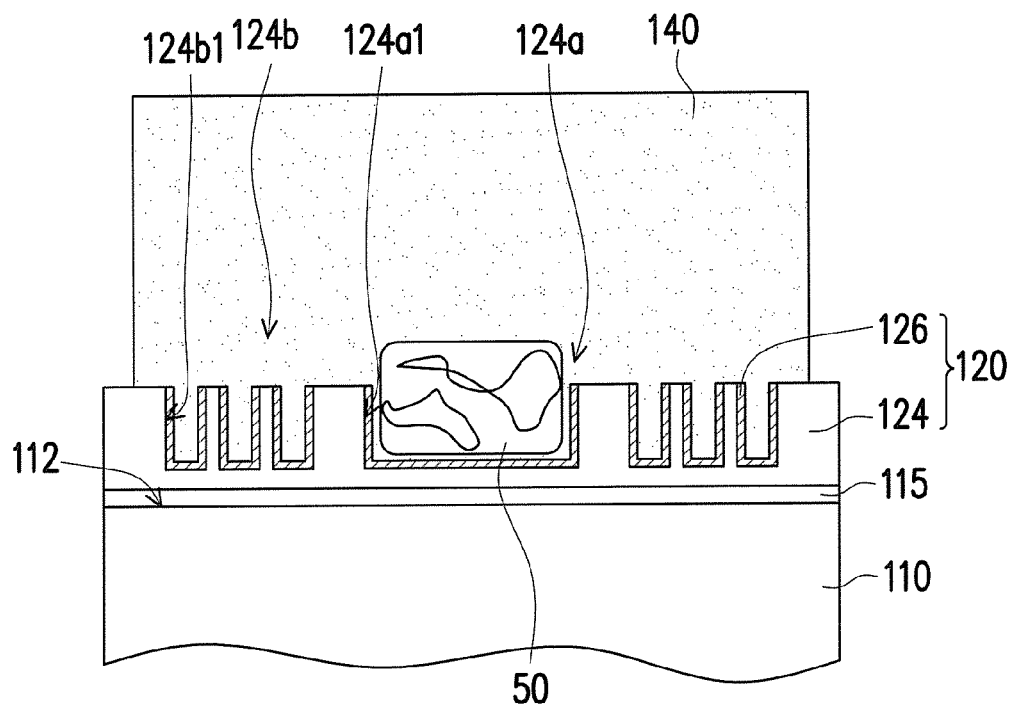

Referring to FIG. 1C, a molding material, such as resin, may be filled between the carrier 120 and the molding plate 130 through the opening 132, so as to form a molding material 140. The molding material 140 covers the sample 50 and is filled into the first groove 124a1 and the second grooves 124b1. Then, as shown in FIG. 1D, the molding material 140 is heated and cured in an environment at the atmospheric pressure or in a vacuum chamber. After the molding material 140 is cured, a release process may be performed to remove the molding plate 130. In this embodiment, the material of the molding material 140 may further include other polymers, such as a photoresist, polyimide (PI), polymethylmethacrylate (PMMA), or an inorganic dielectric material, such as silicon oxide, silicon nitride, or the like, in addition to resin.

Figure 1E:
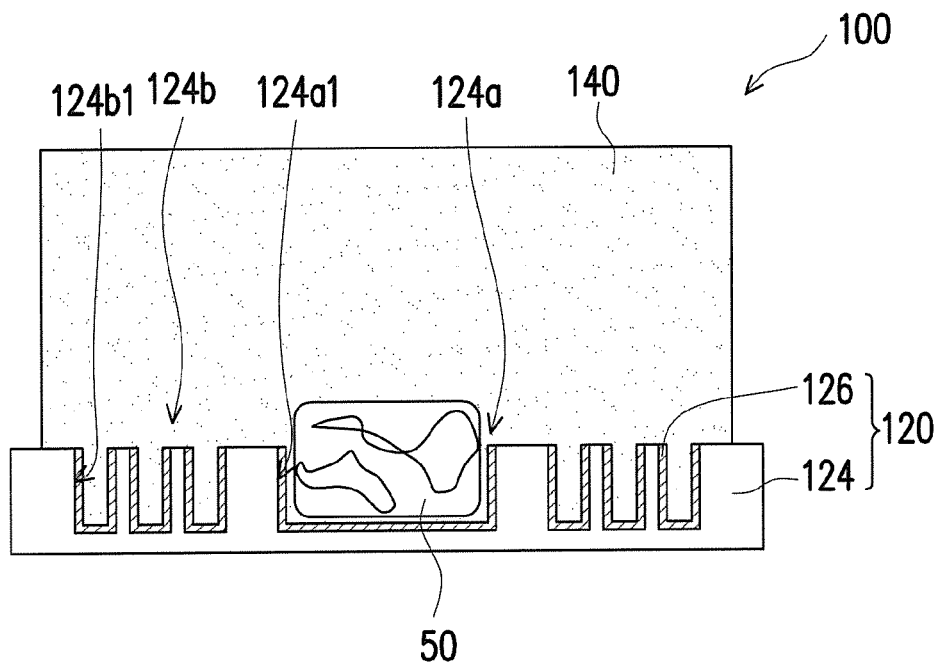

Referring to FIG. 1E, the substrate 110 may be released by means of the release layer 115 and thus removed from the bottom of the carrier material layer 124, so as to obtain the embedded block 100. Then, referring to FIG. 1F, a bottom surface of the embedded sample block 100 may be polished to a position indicated by a cross-sectional line AA' shown in FIG. 1F, so as to expose a portion of the sample 50 and a portion of the marking layer 126 on surfaces of the first groove 124a1 and the second grooves 124b1 at the bottom of the embedded sample block 100. In this embodiment, the portion of the marking layer 126 exposed at the bottom of the embedded sample block 100 may serve to mark a boundary of the sample accommodating area 124a and form a plurality of marks in the marking area 124b.

In this embodiment, the process of releasing the substrate 110 by means of the release layer 115 may include applying ultrasonic oscillation, thermal shock, or mechanical force, or etching the release layer 115 with a chemical solution and removing the substrate 110 by polishing or etching.

Figure 1F:
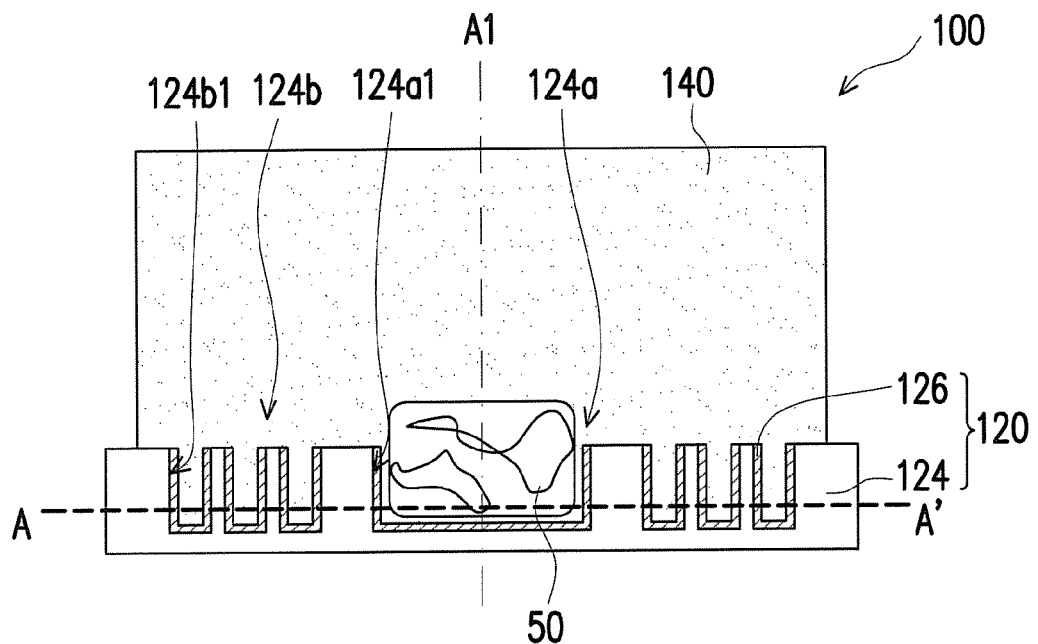
Figure 1G:
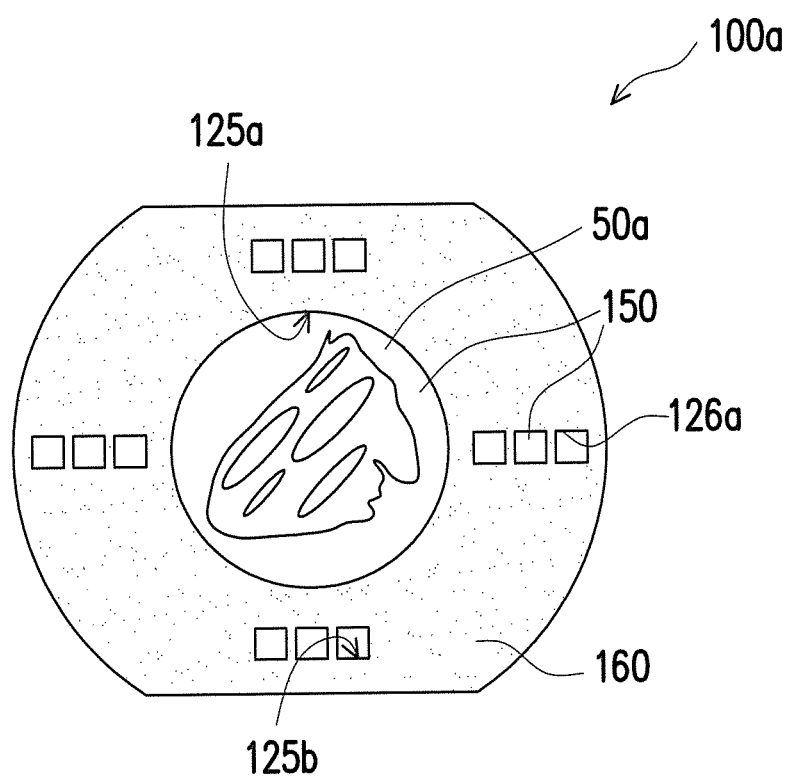

As shown in FIG. 1G, in this embodiment, the molding material 140 with the embedded sample block 100 may serve as a holding part of a slicing machine, so as to hold the embedded sample block 100 in the machine for slicing and thereby generate a plurality of sample sheets 100a. The sample sheet 100a of this embodiment includes a carrying part 160, a sample slice 50a, and a molding part 150. In this embodiment, the carrying part 160 has an accommodating hole 125a corresponding to the first groove 124a1, and marking holes 125b corresponding to the second grooves 124b1. Besides, the sample slice 50a is disposed in the accommodating hole 125a, and the molding part 150 is respectively filled in to the accommodating hole 125a and the marking holes 125b.

In this embodiment, before observing a sample with an electron microscope, the sample may be preserved as a semi-finished product of the embedded sample block 100. Then, when the sample 50 is to be observed with the electron microscope, the embedded sample block 100 may be sliced into a plurality of sample sheets 100a for subsequent observation. In other embodiments, before observing a sample with the electron microscope, a plurality of template semi-finished products of the carrier 120 may be manufactured, so that when a new sample is available for observation, the new sample may be directly embedded into the carrier plate 120 that is already manufactured, so as to shorten the overall time for manufacturing the embedded sample block 100.

Specifically, referring to FIGS. 1F and 1G, the embedded sample block 100 has an axis A1 perpendicular to a surface of the carrier 120, and the embedded sample block 100 may be sliced at a plurality of positions on the axis A1, so as to form the plurality of sample sheets 100a. Therefore, each sample sheet 100a is consistent with a cross-sectional profile of the embedded sample block 100 at the corresponding position on the axis A1.

An extending direction of the marking layer 126 of the polished embedded sample block 100 is parallel to a direction of the axis A1. In addition, after the embedded sample block 100 is sliced, the cut marking layer 126 may form corresponding marking rings 126a in the marking holes 125b. Moreover, since the marking holes 125b of each of the sample sheets 100a are formed in correspondence with the second grooves 124b1 of the embedded sample block 100, layouts of the marking holes 125b and relative positions between the marking holes 125b and the sample slices 50a of the respective sample sheets 100a are the same.

Figure 2A:
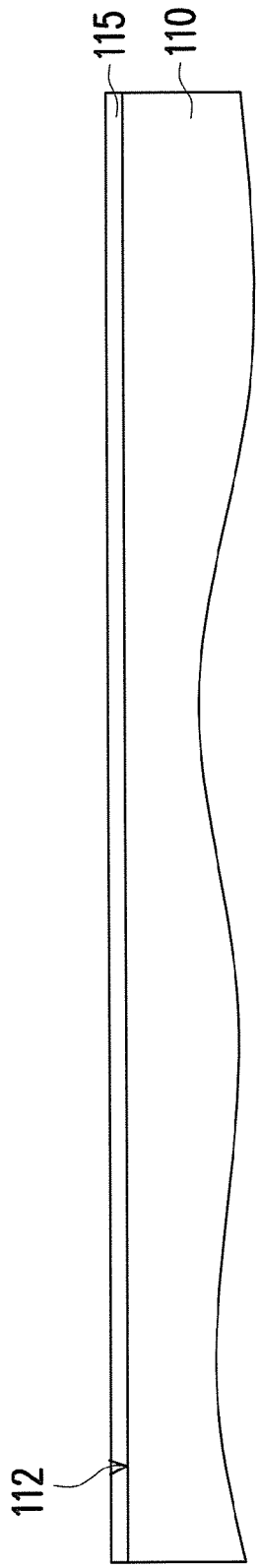
Figure 2B:
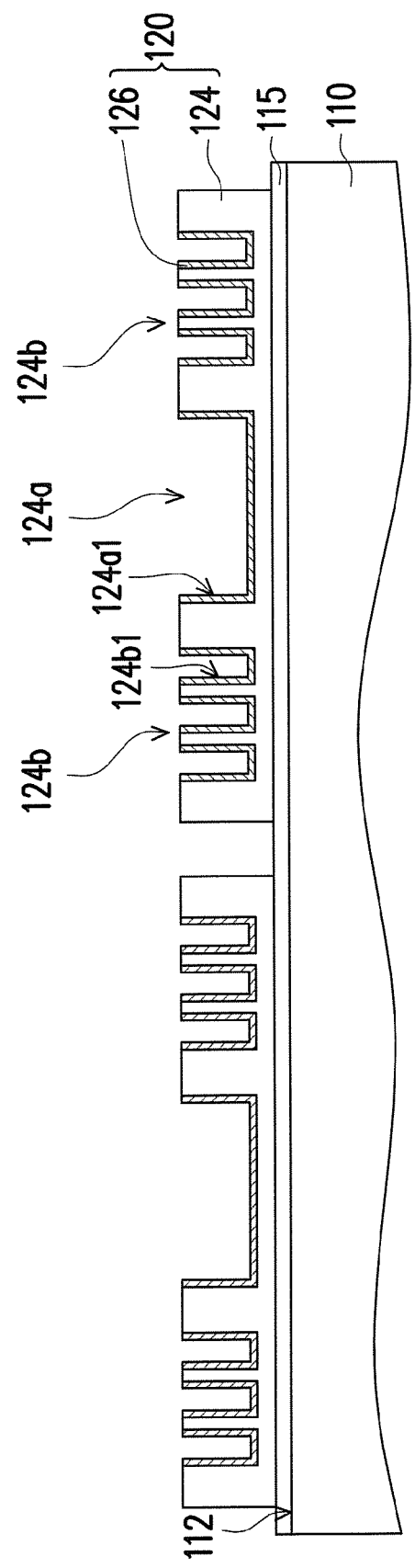
Figure 2G:
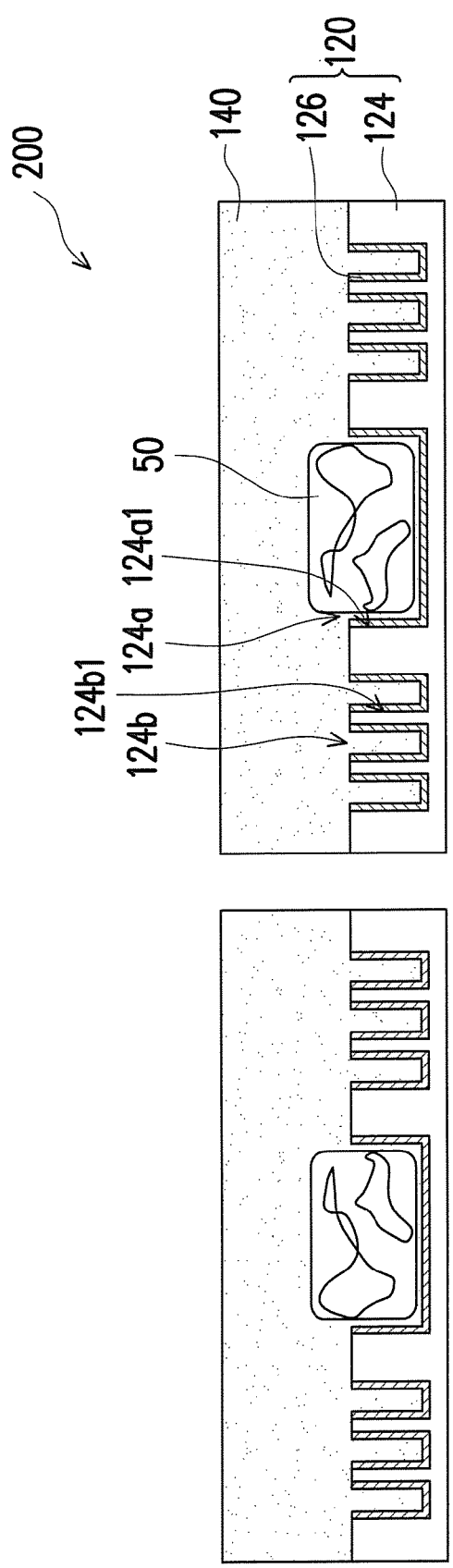

FIGS. 2A to 2G are schematic views illustrating a manufacturing method of an embedded sample block according to another embodiment of the disclosure. The method of manufacturing the embedded sample block of this embodiment differs from the method of manufacturing the embedded sample block shown in FIGS. 1A to 1G in that, in the manufacturing method shown in FIGS. 1A to 1G, only one embedded sample block 100 is manufactured, while in the manufacturing method of this embodiment, a plurality of embedded sample blocks are manufactured at the same time. Referring to FIGS. 2A and 2B, the manufacturing method of this embodiment includes: forming the release layer 115 and the carrier material layer 124 on the upper surface 112 of the substrate 110. In this embodiment, the material of the substrate 110 includes a silicon wafer, for example, and the material of the release layer 115 includes an aluminum layer, for example.

Then, as shown in FIG. 2B, a plurality of carriers 120 (FIG. 2B illustrates two carriers for an illustrative purpose) are formed on the release layer 115. In addition, each carrier 120 includes the sample accommodating area 124a and the marking area 124b. The sample accommodating area 124a includes the first groove 124a1, and the marking area 124b includes the second grooves 124b1. Besides, the marking layer 126 may be formed on the surfaces of the first groove 124a1 and the second grooves 124b1. Referring to FIG. 2C, a plurality of the samples 50 may be respectively disposed into the first grooves 124a1 of the sample accommodating areas 124a.

Referring to FIG. 2D, in this embodiment, molding templates 230 may be aligned to and disposed around and between two parallel carriers 120. In addition, an extending direction of the molding plates 230 is perpendicular to the surface of the substrate 110. In addition, the molding plates 230 surround the carriers 120 and form openings 232.

Then, as shown in FIG. 2E, resin is filled into the openings 232, and the resin is heated and cured to form the molding materials 140. The molding materials 140 cover the carrier material layers 124 and cover the samples 50, and are filled into the first grooves 124a1 and the second grooves 124b1.

Referring to FIG. 2F, after the molding materials 140 are cured, a release process is performed to remove the molding plates 230. Then, referring to FIG. 2G, by removing the substrate 110 by means of the release layer 115, a plurality of embedded sample blocks 200 are obtained at the same time.

In this embodiment, the plurality of embedded sample blocks 200 may be manufactured at the same time by batch manufacturing. Thus, compared with the manufacturing method of FIG. 1 which manufactures one sample block 100, the efficiency of manufacturing the embedded sample blocks 200 according to the embodiment is effectively increased. Besides, the qualities of the embedded sample blocks 200 manufactured in the same batch may tend to be consistent, thereby preventing the inconsistency of qualities among different embedded sample blocks 200.

In this embodiment, the embedded sample blocks 200 may be manufactured by using a silicon wafer material for a semiconductor or micro-electromechanical element as the substrate 110 and performing a related manufacturing process. In this way, the manufacturing quality and precision of the embedded sample block 200 can be effectively improved, and the semi-products of the embedded sample blocks 200 and the carriers 124 may be conveniently manufactured and preserved in advance, so as to shorten the overall procedure and time for preparing the embedded sample blocks 200, or to prepare the sample sheets 100a in batch when the samples 50 are to be observed with the electron microscope.

Figure 3A:
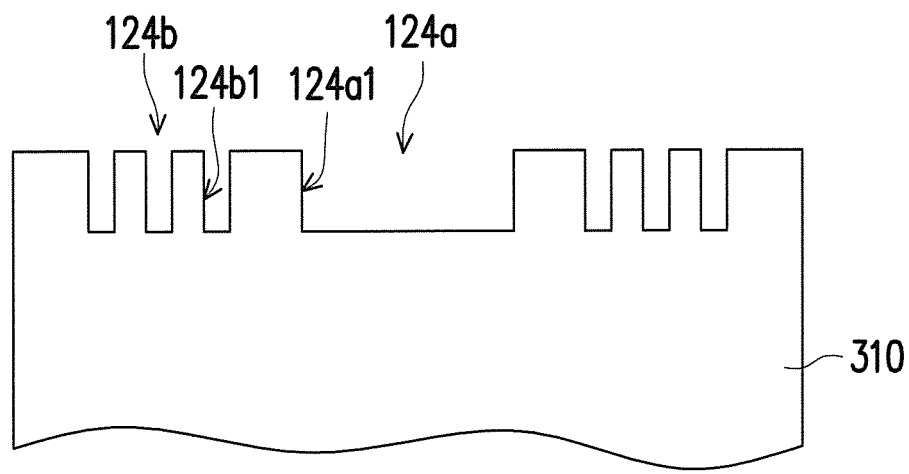
FIGS. 3A to 3E are schematic views illustrating a manufacturing method of an embedded sample block according to yet another embodiment of the disclosure.
Figure 3B:
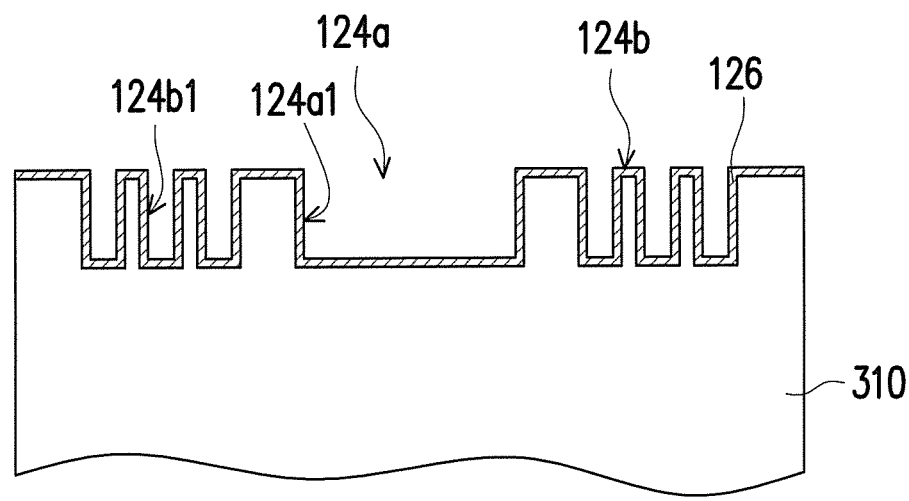

FIGS. 3A to 3E are schematic views illustrating a manufacturing method of an embedded sample block according to yet another embodiment of the disclosure. Referring to FIGS. 3A to 3E, a manufacturing method of an embedded sample block 300 of this embodiment differs from the aforementioned embodiments in that, in the manufacturing method of the embodiment, a resin block is directly used as a substrate 310 of the embedded sample block 300 (as shown in FIG. 3A). In addition, as shown in FIG. 3B, the sample accommodating area 124a and the marking area 124b as well as the first groove 124a1 and the second grooves 124b1 of this embodiment may be directly formed on a surface of the substrate 310.

Specifically, in this embodiment, the sample accommodating area 124a and the marking area 124b of the substrate 310 may be directly formed by performing a treatment process, for example, such as an etching process. Besides, the marking layer 126 may be formed on the surfaces of the first groove 124a1 and the second grooves 124b1 of the sample accommodating area 124a and the marking area 124b by performing an evaporation process.

Figure 3C:
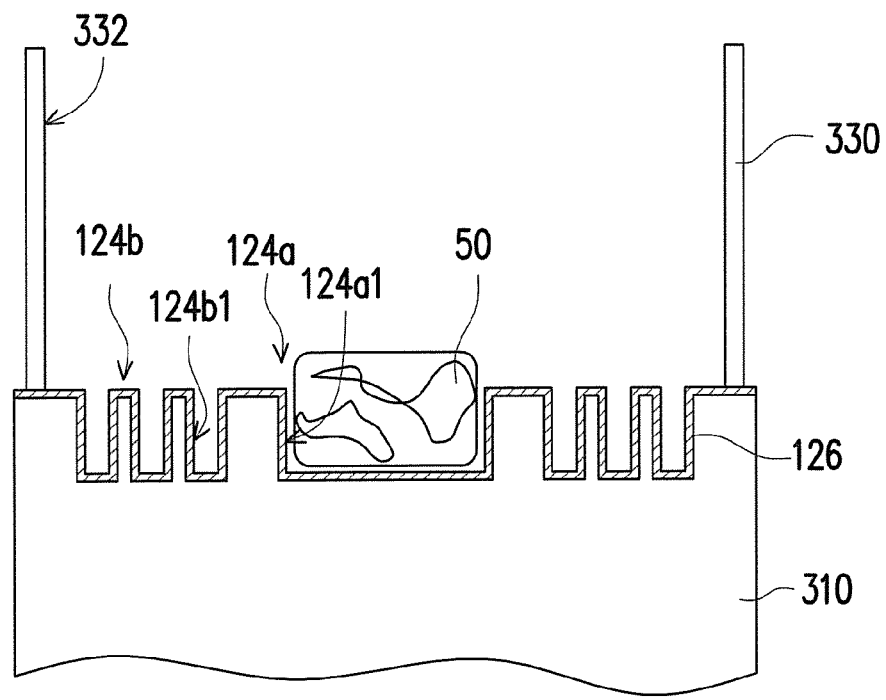
Figure 3D:
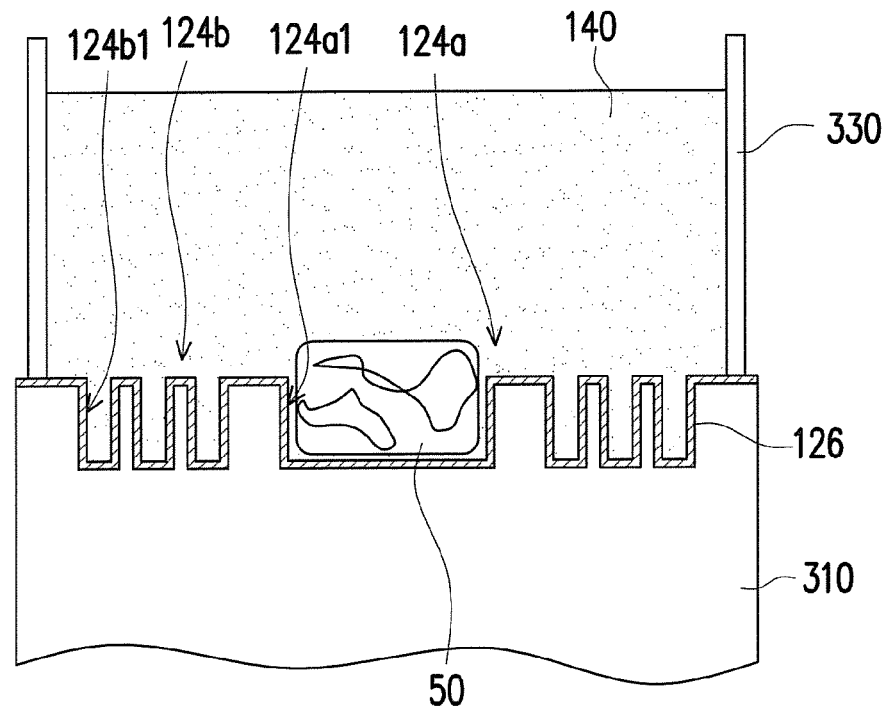

Then, as shown in FIG. 3C, the sample 50 is disposed in the sample accommodating area 124a, and a molding plate 330 is disposed on the substrate 310 and surrounds the sample 50, the sample accommodating area 124a, and the marking area 124b around the substrate 310, so as to form an opening 332. Then, as shown in FIG. 3D, resin is filled into the opening 332 to form the molding material 140.

Figure 3E:
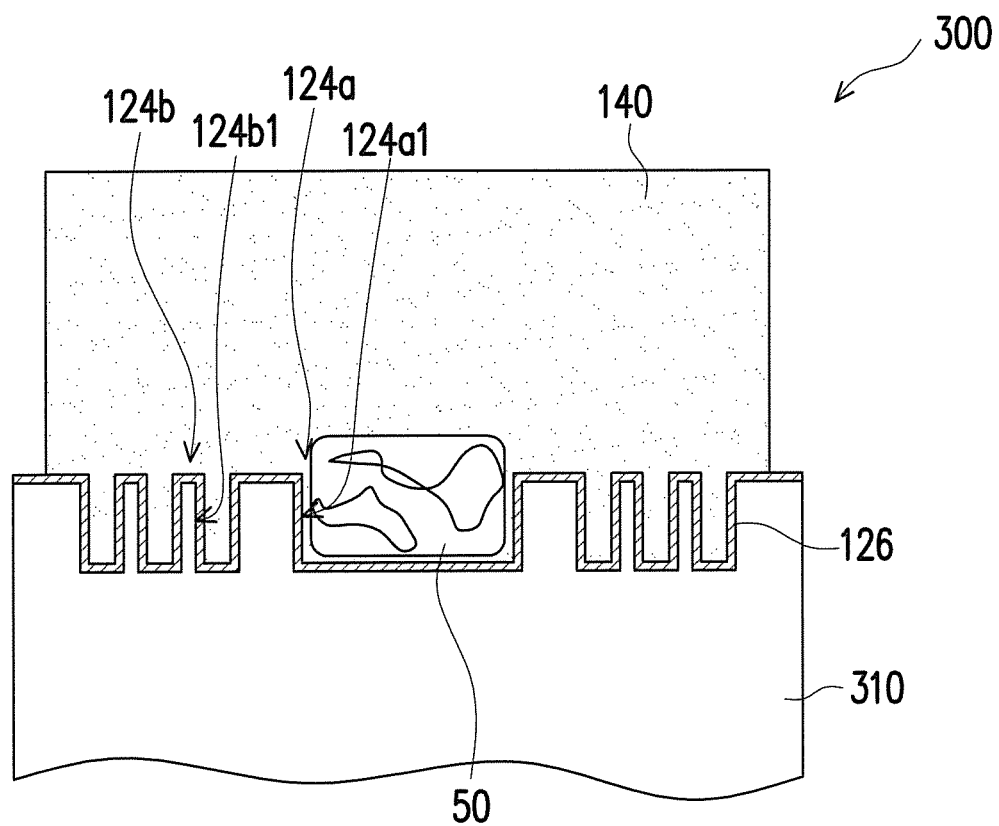

Referring to FIG. 3E, the molding material 140 may be heated and cured in an environment at the atmospheric pressure or in a vacuum chamber. After the molding material 140 is cured, the molding plate 330 is removed, so as to obtain the embedded sample block 300. It should be noted that, when the molding material 140 is heated and cured in the environment of a vacuum chamber, an issue that bubbles are embedded in the molding material 140 may be reduced.

In this embodiment, the manufacturing method of the embedded sample block 300 includes, for example, forming the substrate 310 by using the resin block, using the substrate 310 as the carrier and processing the surface of the substrate 310, such that the sample accommodating area 124a and the marking area 124b may be directly formed on the substrate 310. Therefore, in this embodiment, the embedded sample block 300 does not require the substrate 310 formed by additionally using a silicon wafer or a glass wafer, for example.

Compared the embodiments above, the manufacturing method of this embodiment does not require the additional formation of the release layer on the surface of the substrate 310. Thus, the materials and steps to manufacture the substrate 310 may be effectively reduced, and the manufacturing cost of the embedded sample block 300 is reduced consequently.

FIGS. 4A to 4F are schematic views illustrating a manufacturing method of a carrier material layer of an embedded sample block according to another embodiment of the disclosure. Referring to FIGS. 4A to 4F, a manufacturing method of an embedded sample block 400 of this embodiment is similar to the manufacturing method of the embodiment shown in FIGS. 1A to 1G. However, as explicated in the following, there are still differences between the embodiment and the foregoing embodiment in terms of the manufacture of the carrier.

Figure 4A:
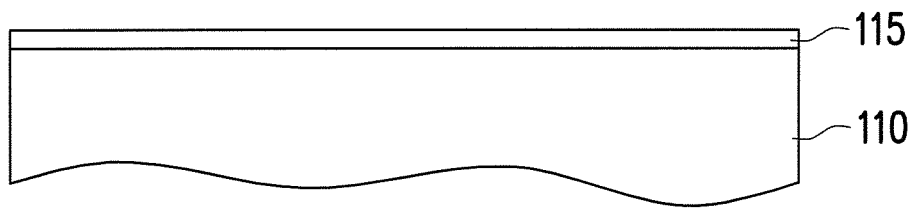
FIGS. 4A to 4F are schematic views illustrating a manufacturing method of a carrier material layer of an embedded sample block according to another embodiment of the disclosure.
Figure 4B:
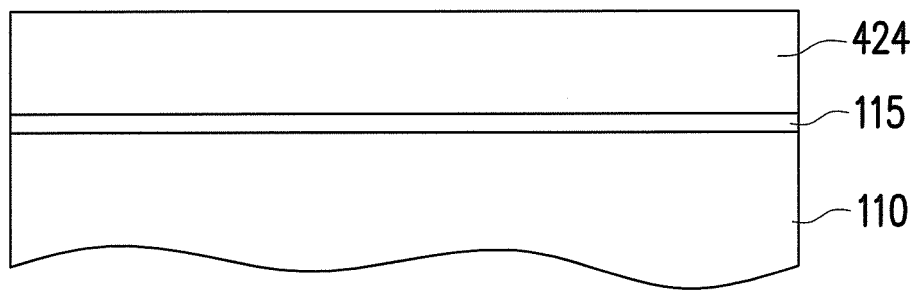
Figure 4C:
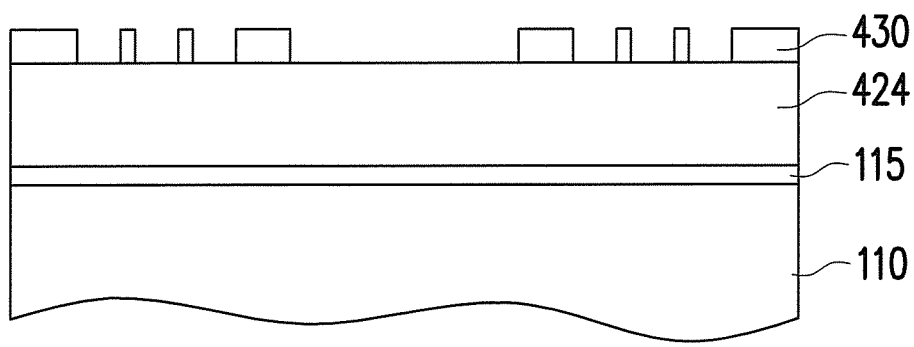

In this embodiment, after the release layer 115 is formed on the surface of the substrate 110 (as shown in FIG. 4A), resin may be coated on a surface of the release layer 115, so as to form a carrier material layer 424 (as shown in FIG. 4B). The carrier material layer 424 is then cured by heating. Then, as shown in FIG. 4C, a photoresist is coated on the carrier material layer 424, and an exposure process and a photolithography process are performed, so as to form a patterned mask 430.

Figure 4D:
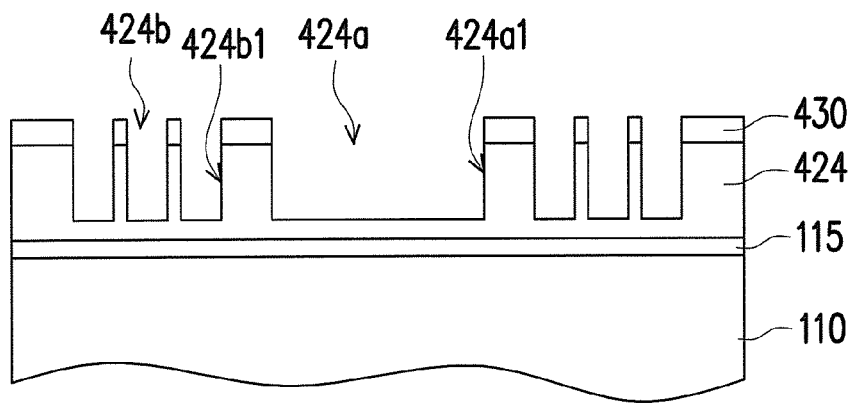
Figure 4E:
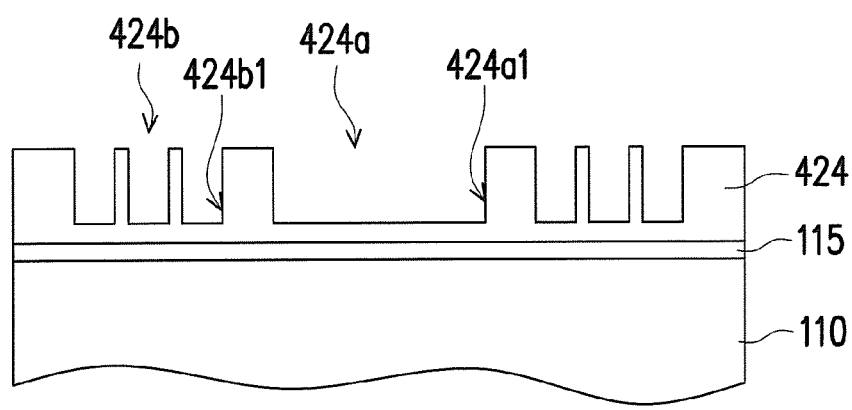
Figure 4F:
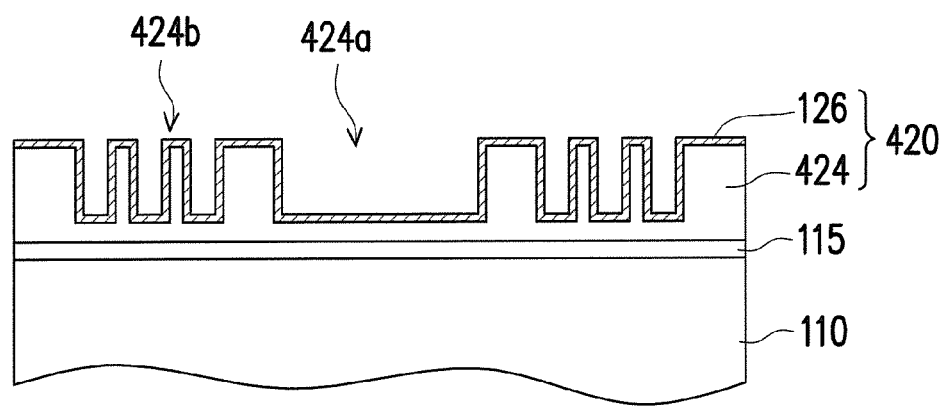

Referring to FIG. 4D, after the patterned mask 430 is formed, an etching process, such as a dry etching process, is performed on the carrier material layer 424 based on a predetermined pattern, so as to form a sample accommodating area 424a and a marking area 424b as well as a first groove 424a1 and second grooves 424b1. Then, as shown in FIG. 4E, the patterned mask 430 is removed, and, as shown in FIG. 4F, the marking layer 126 is formed on the carrier material layer 424 by performing a sputtering process. The material of the marking layer 126 includes a gold layer or an aluminum layer, for example. Accordingly, the manufacture of the carrier 420 is completed.

In this embodiment, the patterned mask 430 may serve as a passivation layer for the carrier material layer 424, so as to define a pattern by performing an etching process. The carrier 420 of this embodiment may be manufactured by performing relevant processes for manufacturing a semiconductor or micro-electromechanical element, so as to facilitate an efficiency and accuracy of manufacturing the carrier 420.

Figure 5A:
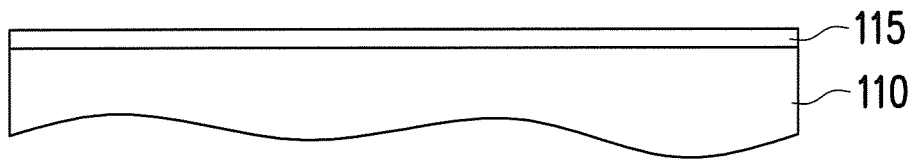
FIGS. 5A to 5H are schematic views illustrating a manufacturing method of a carrier material layer of an embedded sample block according to yet another embodiment of the disclosure.
Figure 5B:
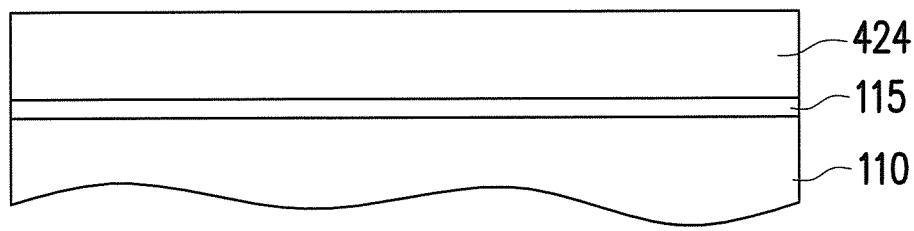
Figure 5C:
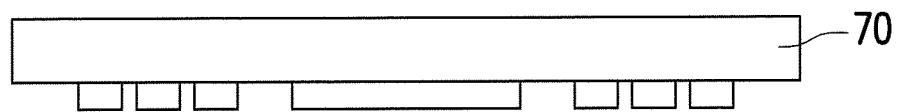

FIGS. 5A to 5H are schematic views illustrating a manufacturing method of a carrier of an embedded sample block according to still another embodiment of the disclosure. In this embodiment, the release layer 115 formed on the substrate 110, as shown in FIG. 5A, and the carrier material layer 424 shown in FIG. 5B are the same as those in the embodiment shown in FIGS. 4A to 4F. Nevertheless, the embodiment still differs from the foregoing embodiment in that the pattern of the carrier material layer 424 is defined by performing a process to imprint a quartz mold core 70 (as shown in FIG. 5C). In this embodiment, a material of the carrier material layer 424 includes a resin layer, for example.

Figure 5D:
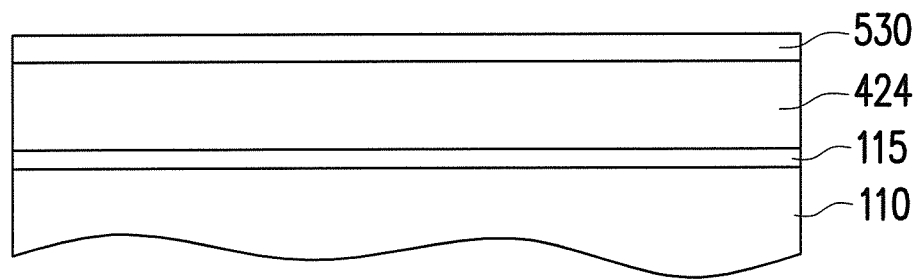
Figure 5E:
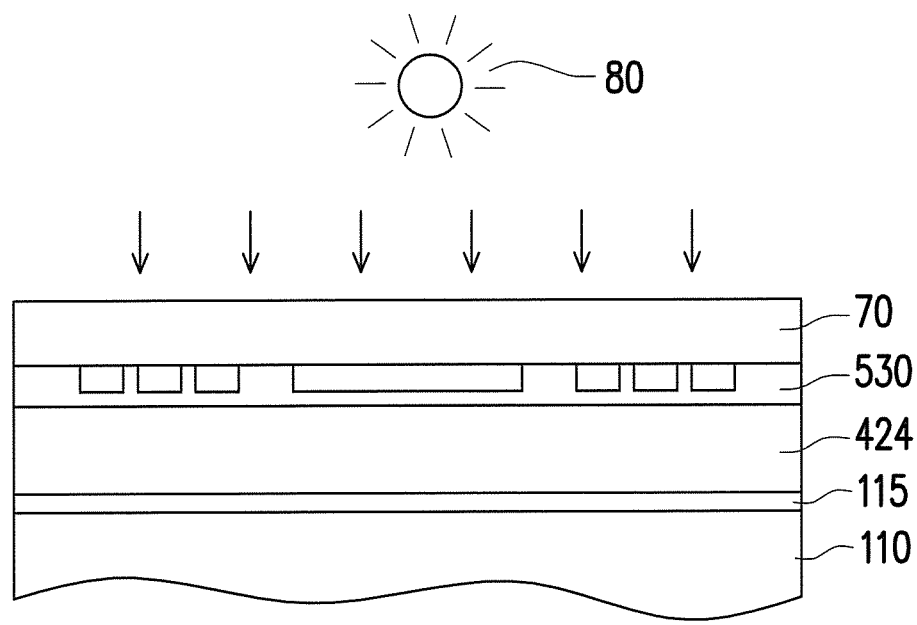
Figure 5F:
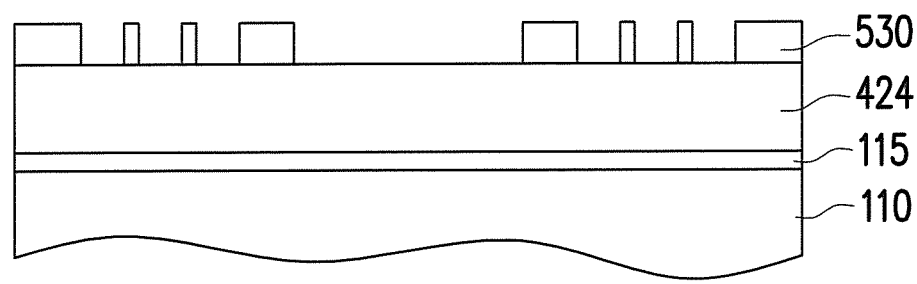

Specifically, referring to FIG. 5D, an ultraviolet (UV) photoresist layer 530 may be coated on a surface of the carrier material layer 424. Then, as shown in FIG. 5E, the quartz mold core 70 is pressed down toward a direction of the UV photoresist layer 530, so as to perform a nano-imprinting process. Meanwhile, an UV light source 80 irradiates the UV photoresist layer 530 along a direction indicated by the arrow sign, so as to cure the UV photoresist layer 530. Then, as shown in FIG. 5F, the quartz mold core 70 is removed, and a patterning process of the UV photoresist layer 530 is completed.

Figure 5G:
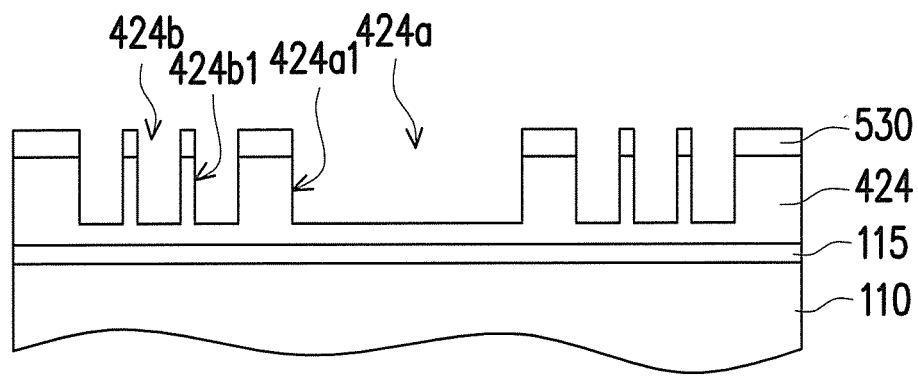

As shown in FIG. 5G, the patterned UV photoresist layer 530 may serve as an etching mask of the carrier material layer 424. In this embodiment, the carrier material layer 424 is patterned by performing a dry etching process, so as to form the sample accommodating area 424a and the marking area 424b as well as the first groove 424a1 and the second grooves 424b1 in the carrier material layer 424.

Figure 5H:
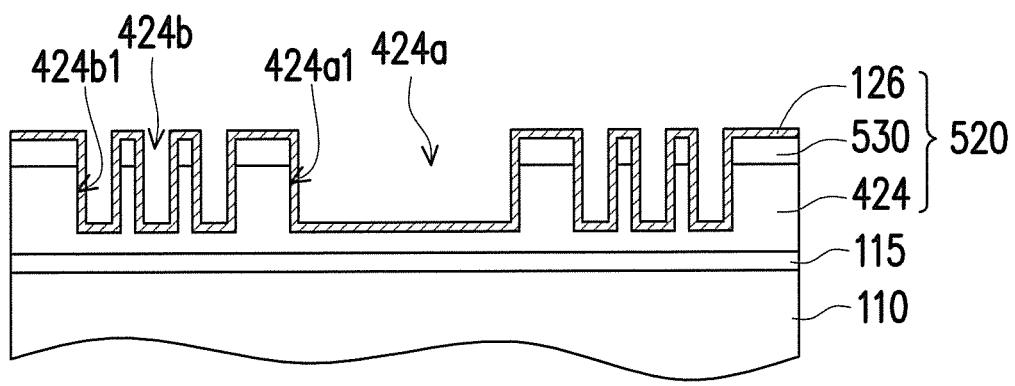

As shown in FIG. 5H, after the carrier material layer 424 is patterned, the marking layer 126 is formed on surfaces of the UV photoresist layer 530, the first groove 424a1, and the second grooves 424b1 by performing a sputtering process. The material of the marking layer 126 includes a gold layer or an aluminum layer. Accordingly, the manufacture of the carrier 520 is completed.

Figure 6:
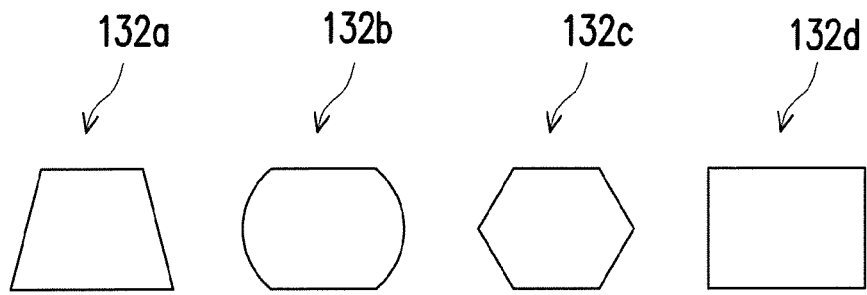
FIG. 6 is a schematic view illustrating shapes of an opening of a molding plate according to an embodiment of the disclosure.

FIG. 6 is a schematic view illustrating shapes of an opening of a molding plate according to an embodiment of the disclosure. Referring to FIGS. 1B and 6, the molding plate 130 may surround the sample 50, the sample accommodating area 124a, and the marking area 124b around the substrate 110, so as to form the opening 132. In this embodiment, based on a structural design of the molding plate 110, the opening 132 may be a trapezoid opening 132a, a doubly-truncated opening 132b, a polygonal opening 132c, or a square opening 132d, as shown in FIG. 6. In this embodiment, since the opening 132 may have different shapes in correspondence with different structural designs of the molding plate 110, the molding material 140 formed in the molding plate 110 may also exhibit different shapes. Thus, the embedded sample blocks 100 in different shapes may be formed. Consequently, when different embedded sample blocks 100 are sliced into sample sheets 100a in different batches, the sample sheets 100a in different batches may exhibit different profiles as marks to indicate the different batches of the sample sheets 100a.

Figure 7A:
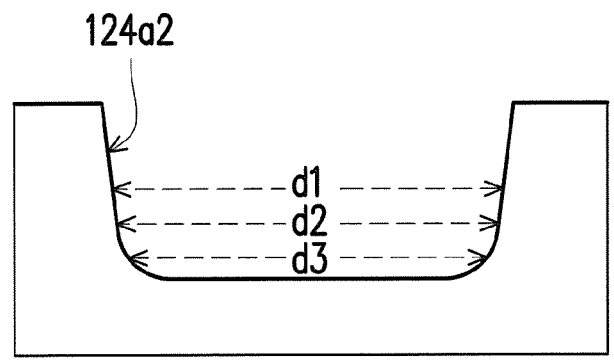
FIG. 7A is a schematic view illustrating a first groove of a carrier material layer according to another embodiment of the disclosure.
Figure 7B:
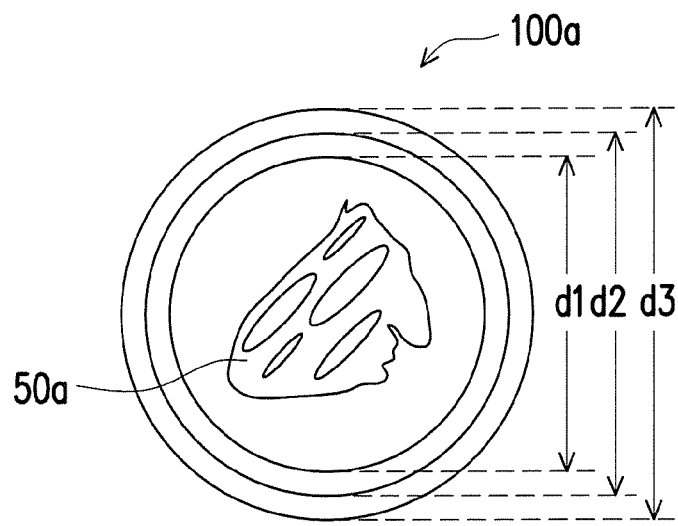
FIG. 7B is a schematic view illustrating a sample sheet from an embedded sample block formed in a first groove of FIG. 7A.

FIG. 7A is a schematic view illustrating a first groove of a carrier according to another embodiment of the disclosure. FIG. 7B is a schematic view illustrating a sample sheet from the embedded sample block formed in a first groove of FIG. 7A. A structure of a first groove 124a2 of this embodiment differs from the structure of the first groove 124a1 in that a sidewall of the first groove 124a1 is perpendicular to a bottom surface of the first groove 124a1, while a sidewall of the first groove 124a2 in this embodiment is inclined with respect to a bottom surface of the first groove 124a2, and an included angle is present between the sidewall and the bottom surface of the first groove 124a2. As shown in FIG. 7A, a shape of the first groove 124a2 of this embodiment from a top perspective is circle, for example, and a diameter of the circle gradually decreases from a top of the groove to a bottom of the groove.

Referring to FIGS. 1G and 7B together, the embedded sample block 100 manufactured by using the first groove 124a2 may be sliced into the plurality of sample sheets 100a having the accommodating holes 125a and the sample slices 50a with diameters d1, d2, and d3 respectively. Therefore, in this embodiment, the same embedded sample block 100 may be sliced to obtain the sample slices 50a having profiles of different sizes. The sizes of the profiles of the sample slices 50a may serve as marks to indicate a sequence of observation on the sample slices 50a. For example, the observation on the sample sheets 100a with the electron microscope may start with the sample sheets 100a whose sample slices 50a have a smaller profile, and the profiles of the sample slices 50a of the sample sheets 100a being observed may gradually increase as an observation procedure proceeds. Thus, the sizes of the profiles of the sample slices 50a may serve to identify a sequential order in the observation of the electron microscope. Besides, to which parts of the embedded sample block 100 different sample sheets 100a belong may also be identified.

Moreover, in an embodiment not shown herein, a cross-sectional width of the first groove 124a2 may also increase from the top of the first groove 124a2 to the bottom of the first groove 124a2. Furthermore, a slope of the sidewall of the first groove 124a2 with respect to the bottom surface of the first groove 124a2 may be properly adjusted according to manufacturing requirements on the sample sheets 100a.

In view of the foregoing, according to the embodiments of the disclosure, the carrier of the embedded sample block has the sample accommodating area and the marking area as well as the first groove and the second groove. In addition, the sample may be placed in the first groove. By using the molding plate disposed on the substrate and the molding material filled into the opening formed by the surrounding molding plate, the embedded sample block having a specific structure may be formed. Besides, different sample sheets with different profiles and shapes may be manufactured by slicing different embedded sample blocks, and the different profiles and shapes may serve as marks to indicate the sample sheets of different batches. Besides, by modifying the slope of the sidewall of the first groove accommodating the sample with respect to the bottom surface of the first groove, the sample accommodating hole with a gradually increasing or decreasing cross-sectional width (diameter) may be produced, such that the sample slices of the sample sheets in the same batch may have different profiles (diameters) serving to identify the sequence of observation of the sample sheets in the same batch. Besides, to which parts of the sample block the different sample sheets belong may also be identified.

In the manufacturing method of the embedded sample block according to the embodiments of the disclosure, the plurality of embedded sample blocks may be manufactured at the same time. In addition, the embedded sample blocks may be manufactured by adopting relevant standardized manufacturing process for a semiconductor or micro-electromechanical element. Therefore, the manufacturing qualities of different embedded sample blocks may become more consistent, so as to increase the efficiency and quality in manufacturing the sample of the electron microscope. Besides, since the sample sheets formed by slicing the embedded sample block are provided with precise alignment marks that are directly manufactured on the sample sheets, the retrieval and placement as well as an automated positioning operation of the sample sheets become easier. Thus, the time required for the electron microscope to position during observation and reorganize the image may be effectively reduced.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:
1. A manufacturing method of an embedded sample block, comprising:
   providing a carrier having a sample accommodating area and a marking area, wherein the sample accommodating area has a first groove, and the marking area has a plurality of second grooves;
   disposing a sample in the first groove;

forming a molding plate standing around the carrier, wherein the molding plate surrounds the sample accommodating area and the marking area and forms an opening exposing the sample, the first groove, and the second grooves;

forming a molding material inside the opening, wherein the molding material covers the sample and is filled into the first groove and the second grooves;

curing the molding material; and removing the molding plate to obtain the embedded sample block.

2. The method as claimed in claim 1, wherein the step of forming the carrier comprises:

providing a carrier material layer on the substrate;

forming a release layer between the carrier material layer and the substrate, such that the carrier material layer is disposed above the substrate with interposition of the release layer;

patterning the carrier material layer to form the first groove and the second grooves; and forming a marking layer covering surfaces of the first groove and the second grooves.

3. The method as claimed in claim 2, wherein the step of patterning the carrier material layer comprises:

forming a patterned mask on the carrier material layer; and etching the carrier material layer by using the patterned mask, so as to form the first groove and the second grooves.

4. The method as claimed in claim 3, wherein the step of forming the patterned mask comprises:

coating a photoresist layer on the carrier material layer;

patterning the photoresist layer; and curing the patterned photoresist layer to form the patterned mask.

5. The method as claimed in claim 2, further comprising polishing a bottom surface of the embedded sample block to expose a portion of the marking layer and form a plurality of marks.

6. The method as claimed in claim 1, wherein the step of forming the carrier comprises:

providing a substrate;

patterning a surface of the substrate to form the first groove and the second grooves; and forming a marking layer covering surfaces of the first groove and the second grooves.

7. The method as claimed in claim 1, further comprising slicing the embedded sample block along an axial direction to form a plurality of sample sheets.

8. The method as claimed in claim 1, wherein the opening is in a trapezoid shape, a doubly-truncated circular shape, or a polygonal shape.

9. The method as claimed in claim 7, wherein a width of the first groove gradually decreases along the axial direction.

10. A sample sheet, obtained by continuously slicing an embedded sample block along an axial direction, wherein profiles of different sample sheets correspond to cross-sectional profiles of the embedded sample block at different positions in the axial direction, so as to determine a sequence of the respective sample sheets, and the embedded sample block comprises:

a carrier, having a sample accommodating area and a marking area, wherein the sample accommodating area has a first groove, and the marking area has a plurality of second grooves;

a sample, disposed in the first groove; and a molding material, covering the sample and filled into the first groove and the second grooves, wherein the sample sheet comprises:

a carrying part, obtained by slicing the carrier and having an accommodating hole corresponding to the first groove and a plurality of marking holes corresponding to the second grooves;

a sample slice, located in the accommodating hole; and a molding part, filled into the accommodating hole and the marking holes.

11. The sample sheet as claimed in claim 10, wherein a width of the first groove of the embedded sample block gradually decreases along the axial direction, and the accommodating holes of different sample sheets have different widths.

12. The sample sheet as claimed in claim 10, wherein profiles of the sample sheets comprise a trapezoid shape, a doubly-truncated circular shape, or a polygonal shape.

13. The sample sheet as claimed in claim 10, wherein the molding material comprises resin.

14. The sample sheet as claimed in claim 10, wherein the carrier comprises a marking layer covering surfaces of the first groove and the second grooves, and the carrying part of the sample sheet has marking rings located in the respective marking holes and corresponding to the marking layer.

15. The sample sheet as claimed in claim 14, wherein the marking holes of the respective sample slices have the same layout.

* * * * *